United States Patent [19]

Tanaka et al.

[11] Patent Number: 4,771,039

[45] Date of Patent: Sep. 13, 1988

[54] BOTULINUS TOXIN NEUTRALIZER

[75] Inventors: Ryuichiro Tanaka, Tachikawa; Koutaro Takamizawa, Irima; Hiroo Takayama, Tokorozawa; Toshizo Sakurai, Mitaka; Mitsuo Mada, Kodaira; Masahiko Mutai, Higashiyamato, all of Japan

[73] Assignee: Kabushiki Kaisha Yakult Honsha, Tokyo, Japan

[21] Appl. No.: 844,026

[22] Filed: Mar. 25, 1986

[30] Foreign Application Priority Data

Mar. 29, 1985 [JP] Japan ................................. 60-63284

[51] Int. Cl.$^4$ .................. A61K 31/70; A61K 31/685; A61K 35/48
[52] U.S. Cl. ........................................ 514/25; 514/78; 514/558; 514/823; 424/105
[58] Field of Search ................... 514/25, 78, 558, 823; 424/105

[56] References Cited

PUBLICATIONS

Chem. Abst. 76(7):31049w, 1972.
Chem. Abst. 76(7):31050q, 1972.
Chem. Absts. 106(5):28693j, 1987.
Chem. Absts. 104(25):223817p, 1986.
Chem. Absts. 103(19):155679x, 1985.
Chem. Absts. 100(15):116176z, 1984.
Chem. Absts. 93(1):1891y, 1980.
Chem. Absts. 93(5):43033a, 1980.
Chem. Absts. 76(7):59290n, 1972.
Chem. Absts. 75(15):96935f, 1971.
Chem. Absts. 84(25):175564y, 1976.

*Primary Examiner*—John Rollins
*Attorney, Agent, or Firm*—Wenderoth, Lind & Ponack

[57] ABSTRACT

A botulinus toxin neutralizer comprising heat-treated fat globule membranes of animal milk or gangliosides isolated from fat globule membranes of animal milk. The neutralizer of the former nature is prepared from a material containing fat globules of animal milk by fractionating the material for separating the membranes of the fat globules from the rest of the material, and subjecting the separated fat globule membranes to heat treatment. The neutralizer of the former nature is prepared from a material containing fat globules by fractionating the material for separating the membranes of the fat globules from the rest of the material, and isolating gangliosides from the globule membranes.

21 Claims, No Drawings

BOTULINUS TOXIN NEUTRALIZER

FIELD OF THE INVENTION

The present invention relates to a botulinus toxin neutralizer which is effective for the prevention and treatment of botulinus intoxication and to a method of preparing such a botulinus toxin neutralizer.

BACKGROUND OF THE INVENTION

Botulinus toxin is a proteinous exotoxin produced by *Clostridium botulinum* and acts on the peripheral nervous system. When ingested by human, the botulinus toxin gives rise to intoxication called botulism which is accompanied by paralytic symptoms. It is well known that the neurotoxin is absorbed from the alimentary tract and acts peripherally at the neuromuscular junctions controlled by the parasympathetic nerves. The toxin thus interferes with the release of acetylcholine from the chlorinergic motor nerve endings and causes botulism. In respect of the mode of action of the botulinus toxin, it has been widely accepted that a certain acidic glycolipid, viz., the ganglioside GT1b present in the neuromembrane acts as a receptor for the toxin. While other gangliosides such as the gangliosides GQ1b and GD1b also have the ability of combining with botulinus toxin, such an ability of these gangliosides is inferior to that of the ganglioside GT1b and, for this reason, it has been considered that the gangliosides GQ1b and GD1b are less responsible for the action to the botulinus toxin.

The treatment of botulism is extremely difficult and, at the present time, there is practically no other method of treatment than to cease the symptoms. It may be presumed that botulism could be treated with use of the ganglioside GTb1 as an antagonist to the botulinus toxin, in view of the mode of action of the toxin as above discussed. The ganglioside GTb1, which thus acts as an antagonistic receptor for the botulinus toxin, will combine with the toxin and will prevent the onset of the toxicity thereof. A problem is however encountered in that the source presently available of the ganglioside GTb1 is none but the bovine brain, which is so expensive that the method of treating botulism with use of such a ganglioside has seldom been put into practice.

Under these circumstances, it is an object of the present invention to provide an economical botulinus toxin neutralizer which can be used as an antagonistic toxin receptor for the treatment of botulism and which will thus facilitate the prevention and treatment of botulism.

It is another object of the present invention to provide a method of preparing such a botulinus toxin neutralizer.

SUMMARY OF THE INVENTION

In the process of studying milk fat globule membranes (MFGM, herein after referred to simply as fat globule membranes) derived from animal milk, the present inventors found that a substance prepared from such membranes had a potent ability of neutralizing botulinus toxin. The present invention has been completed on the basis of this discovery and, in accordance with a first outstanding aspect of the present invention, there is provided a botulinus toxin neutralizer (hereinafter referred to as a neutralizer according to the first aspect of the present invention) comprising heat-treated fat globule membranes of animal milk. In accordance with another outstanding aspect of the present invention, there is provided a botulinus toxin neutralizer (hereinafter referred to as a neutralizer according to the second aspect of the present invention) comprising gangliosides isolated from fat globule membranes of animal milk.

In accordance with still another outstanding aspect of the present invention, there is provided a method of preparing a botulinus toxin neutralizer from a material containing fat globules of animal milk, comprising the steps of
(a) fractionating the material for separating the membranes of the fat globules from the rest of the material, and
(b) subjecting the separated fat globule membranes to heat treatment.

In accordance with still another outstanding aspect of the present invention, there is provided a method of preparing a botulinus toxin neutralizer from a material containing fat globules, comprising the steps of
(a) fractionating the material for separating the membranes of the fat globules from the rest of the material, and
(b) isolating gangliosides from the globule membranes.

Where animal milk is used as the starting material, the fat globule membranes may be separated from the rest of the animal milk by fractionating the animal milk to separate cream from the rest of the animal milk, washing the cream to remove impurities therefrom, churning the resultant cream to separate the cream into buttermilk and butter granules, and fractionating the buttermilk to separate the globule membranes from the rest of the buttermmilk.

DESCRIPTION OF THE PREFERRED EMBODIMENTS

As will be described in more detail, a botulinus toxin neutralizer according to the first aspect of the present invention is prepared through heat treatment of fat globule membranes of animal milk. When the gangliosides present in such a neutralizer or a semi-processed product of the neutralizer are isolated from the fat globule membranes, there results a botulinus toxin neutralizer according to the second aspect of the present invention.

The fat globule membranes of animal milk are the membranes covering the fat globules of the milk and are formed while the milk fats are being excreted into the mammary gland. The membranes are similar in chemical composition to the membranes of the mammary gland cells and are about 10 nm thick on the fat globules which measure about 1 to 10 microns in diameter in the case of bovine milk. The major constituents of such fat globule membranes include phospholipids, enzymes, proteins, glycoproteins, triglycerides, cholesterols and so forth. Among these constituents of the membranes, proteins and lipids alone account for more than 90% of the total amount with the proteins accounting for 45% and the lipids accounting for 55% of the protein and lipid fraction. Six types of gangliosides have thus far been found present in the lipids and contained in amounts totalling about 6 nano mols (in terms of sialic acid equivalent) per 1 mg of protein. These six types of gangliosides include the ganglioside GD3, GM2 and GM3 of which the ganglioside GD3, in particular, is the most prevalent. It may be noted that the ganglioside GT1b, which is known to be a possible antagonistic botulinus toxin receptor as previously discussed, has not been found to be included among the six gangliosides.

Description will now be made regarding a method of preparing a botulinus toxin neutralizer according to the first aspect of the present invention.

As the starting material for the preparation of such a toxin neutralizer may be used the buttermilk fraction of animal milk which can be readily and economically obtained as a byproduct of a buttermaking process. In an ordinary buttermaking process, cream is prepared by centrifuging animal milk and butter granules are produced when the cream is churned. Fat globule membranes are concentrated in the buttermilk fraction which is left with the butter granules separated from the churned cream. The buttermilk fraction is then processed to separate the fat globule membranes from the rest of the buttermilk. The fat globule membranes thus obtained are heated preferably after they are purified, lyophilized and/or disintegrated into debris in appropriate manners. The substance which results from this heat treatment is a neutralizer according to the first aspect of the present invention.

A method according to the present invention can thus be most advantageously put into practice using the buttermilk fraction of animal milk as the starting material. It should however be borne in mind that the use of such a starting material is not limitative of the present invention. If desired, a method according to the present invention may otherwise be carried out with use of, for example, a suitable equivalent of buttermilk. Such a buttermilk equivalent may be obtainable by adding water to cream of animal milk, centrifuging the resultant mixture for cleaning the cream, and thereafter churning the cream.

Buttermilk or any fraction of animal milk similar in chemical composition to buttermilk is excessively abundant with such milk components as the milk proteins and lactose and is, as it is, not suitable for use as a starting material for the preparation of a toxin neutralizer according to the first aspect of the present invention. It is for this reason preferable that the fat globule membranes separated from the buttermilk or a similar fraction of animal milk be purified by the use of, for example, dialysis, ammonium sulfate fractionation, gel filtration, isoelectric-point precipitation or any other appropriate method. Because, in addition, of the fact that fat globule membranes in general contain various enzymes such as alkali phosphatase, xanthine oxidase and acid phosphatase, it is necessary to have the enzymes inactivated by heating the fat globule membranes after the membranes are thus purified. This heat treatment may be performed by, for example, heating the globule membranes at 62° C. for more than 30 minutes or by using a heating step tantamount to a U.H.T.S.T. (ultra-high-temperature short-time) pasteurization method. As well known in the art, a U.H.T.S.T. pasteurization process uses a heating temperature higher than 100° C. for a short period of time.

The fat globule membranes which have thus been processed may include those having sizes approximately equal to the sizes which the membranes had on the intact fat globules. Such globule membranes tend to precipitate when dispersed in water for the cleaning by centrifuging. It is for this reason preferable that the fat globule membranes which have been purified as discussed above be ultrasonicated into fine debris to form a stable suspension in water before the membranes are subjected to the heat treatment.

The fat globule membranes which have received all the described treatment steps may be lyophilized for later use, or may be otherwise processed by any desired method to produce a pharmaceutical version of a toxin neutralizer according to the first aspect of the present invention. If desired, the fat globule membranes which may be obtained in the form of powder by the disintegration and lyophilization steps may be per se utilized as a toxin neutralizer.

A toxin neutralizer according to the second aspect of the present invention can be prepared by isolating gangliosides from a toxin neutralizer according to the first aspect of the present invention or from a semi-processed product of the neutralizer. Any desired method may be used for the isolation of the gangliosides from the neutralizer or the semi-processed product thereof. One method is to use a mixture of chloroform and methanol as a solvent for extracting lipids from the fat globule membranes and thereafter separate gangliosides from the extracted lipids by a gel filtration method. The ganglioside fraction thus obtained consists of a mixture of six types of gangliosides as stated previously. Regarding these gangliosides, it has not been determined whether all of the six types of gangliosides form the essential components of a toxin neutralizer according to the present invention or only one or more of the gangliosides are effective as such. Where it is desired that the gangliosides thus extracted be further fractionated for refining purposes, it is for this reason important that the fractionation be effected in consideration of the degree of the ability which each of the ganglioside fractions should have for inactivating the botulinus toxin. If the gangliosides are to be refined simply for desalting purposes, either the dialysis or treatment with ion-exchange resin will suit the purposes.

The toxin inactivation ability of a botulinus toxin neutralizer according to the present invention depends on the kind of the animal milk used as the starting material and varies from one animal milk to another. It would for this reason be of no significance to specify a standard unit quantity in which a botulinus toxin neutralizer according to the present invention should be used on a practical basis. Ordinarily, it is advisable for a user of the neutralizer to determine the toxin inactivation ability of a particular neutralizer for a particular case by, for example, a testing method set forth in the Examples to be described and to specify the proper unit quantity in which the neutralizer should be used for the particular case. It may however be mentioned for estimation purposes that, where the neutralizer is to be used for the treatment or prevention of botulism through oral administration, an appropriate dose of the neutralizer will ordinarily range from about 4 mg to about 100 mg for a toxin neutralizer according to the first aspect of the present invention and from about 2 mg to about 500 mg for a toxin neutralizer according to the second aspect of the present invention (per day for an adult).

A botulinus toxin neutralizer provided in accordance with the present invention may be used not only for oral administration but also as an additive to a gastrointestinal washing fluid or to food. Furthermore, a toxin neutralizer according to the second aspect of the present invention, in particular, may also be used in combination with a botulinus toxin antiserum for injection into the blood.

Analysis will now be made into the mode of action of a botulinus toxin neutralizer according to the present invention. When the neutralizer is introduced into the body, all or some of the gangliosides contained in the neutralizer encounter the botulinus toxin and act as antagonistic receptors binding to the toxin. It therefore follows that the toxin is precluded from combining with the cellular tissues at the active site of human body and is thus excreted without acting on the site. When used as an additive to food, the neutralizer binds to the toxin produced by *Clostridium botulinum* in the food and inactivates the toxin.

A toxin neutralizer according to the present invention is advantageous firstly in that it can be manufactured from the buttermilk which is readily and economically available in the form of a concentrate as a byproduct of buttermaking. Such a starting material merely requires simple fractionation and heat treatment steps or fractionation and isolation steps for being manufactured into a toxin neutralizer. The toxin neutralizer is thus more adapted for production on a large-scale commercial basis and is lower in production cost than existing globule membrane products prepared from bovine brains. Furthermore, a toxin neutralizer according to the present invention is manufactured simply through the fractionation and heat treatment or through the fractionation and isolation of animal milk without involvement of chemical processing of the material and is therefore fully acceptable from the safety point of view.

As will be appreciated from the foregoing description, a botulinus toxin neutralizer according to the present invention will open up the way anew for the treatment of botulism which has long been coped with merely by ceasing the symptoms. A toxin neutralizer according to the present invention will also contribute to the prevention of botulism by, for example, addition of the neutralizer to food or the like.

The present invention will be hereinafter described in more detail in the following Examples of a method according to the present invention.

EXAMPLE 1

One liter of bovine milk containing 3.3% of fat was centrifuged at 3,000 rpm for 15 minutes to obtain cream thereof. The cream was centrifuged to wash the fat globules to remove water-soluble impurities therein with water added to give a total volume of 440 ml, the washing steps being repeated further three times. The cream containing the fat globules cleaned by this centrifuging step was allowed to stand at 4° C. overnight and was churned to separate into buttermilk and butter granules. The buttermilk was made up with ammonium sulfate to 50% saturation and was allowed to stand overnight followed by centrifugation at 3,000 rpm for 30 minutes. Thereafter, the floating fat globule membranes were taken into water to make a suspension, which was then dialyzed against distilled water at 4° C. The resultant preparation was centrifuged at 10,000 rpm for 30 minutes to precipitate fat globule membranes. The fat globule membranes thus precipitated were lyophilized, whereby 650 mg of dried fat globule membranes were finally obtained.

Subsequently, the dried fat globule membranes were suspended in water, followed by ultrasonication of the suspension to disintegrate the membranes into fine debris. The resultant preparation containing the disintegrated fat globule membranes was heated at 100° C. for 30 minutes for inactivating the undesired enzymes which are likely to have strayed into the membranes. A toxin neutralizer was thus obtained as an example of a neutralizer according to the first aspect of the present invention.

Thirty mg of this botulinus toxin neutralizer was dissolved into 1.5 ml of Tris-chloride buffer solution (0.01M, pH 7.2). The resultant solution was allowed to react with 2 $\mu$g of purified type A botulinus toxin at 37° C. for 30 minutes to determine the amount of residual toxin by a toxin inactivation ability test. This toxin inactivation ability test was conducted by the known time-to-death method using intravenous injection into mice (Japan J. Bacteriology, Vol. 92, No. 5, 1980). The amount of residual toxin was thus determined to be less than 0.9%, showing that the botulinus toxin used was almost completely neutralized.

EXAMPLE 2

Dried fat globule membranes were obtained folowing the procedure taken in Example 1. Whole lipids were extracted from 1.0 g of fat globule membranes using 20 ml of chloroform/methanol (2:1, v/v) and 10 ml of chloroform/methanol (1:1, v/v). The lipids thus obtained were fractionated into neutral lipid and glycolipid fractions with use of Sephadex A-25 column (of the acetate form). The glycolipids were chemically neutralized with addition of weak alkali, followed by desalting by dialysis and subsequent treatment with an ion-exchange resin. The resultant preparation was lyophilized to obtain 0.8 mg of toxin neutralizer as an example of a neutralizer according to the second aspect of the present invention. This toxin neutralizer (4.7 g) was allowed to react with purified type A botulinus toxin, whereupon a toxin inactivation ability test as used in Example 1 was conducted to determine the amount of residual toxin, which was also found to be less than 0.9%.

For purposes of comparison, a similar toxin inactivation ability test was conducted with 50 $\mu$g of a commercially available ganglioside mixture (Sigma Type II, consisting of 20% of GM1, 40% of GD1a, 20% of GD1b and 20% of GT1b). The test proved that there was 9.0% of residual toxin.

EXAMPLE 3

One liter of goat milk containing 4.25% of fat was centrifuged at 3,000 rpm to obtain cream thereof. The cream was centrifuged for washing the fat globules therein with water added to give a total volume of 570 ml, the washing steps being repeated further three times. The cream containing the fat globules thus cleaned was allowed to stand at 4° C. overnight and was subjected to churning to separate into buttermilk and butter granules. The buttermilk was then heated at 100° C. for 10 minutes and was thereafter dialyzed against distilled water at 4° C. The fat globule fraction resulting from the dialysis was lyophilized to obtain 760 mg of dried fat globule membranes as an example of a toxin neutralizer according to the first aspect of the present invention.

The dried fat globule membranes were processed following the steps taken in Example 2, with the result that 302 $\mu$g of toxin neutralizer was obtained as an example of a toxin neutralizer according to the second aspect of the present invention. Using a toxin inactivation ability test as used in Example 1, 4.5 $\mu$g of this neutralizer was tested to determine the amount of residual toxin, which was found to be 36%.

EXAMPLE 4

Toxin inactivation ability tests for type B and type E botulinus toxins were further conducted using two different types of ganglioside preparation. One type of ganglioside preparation was prepared from bovine milk following the steps of Example 1 as an example of a neutralizer according to the first aspect of the present invention. The other type of ganglioside preparation was prepared from commerically available buttermilk (manufactured by Snow Brand Milk Products Co., Ltd., Tokyo). To prepare the latter type of ganglioside preparation from the commercially available buttermilk, whole lipids were extracted from 1.0 g of the buttermilk using 20 ml of chloroform/methanol (2:1, v/v) and 10 ml of chloroform/methanol (1:1, v/v). The lipids thus extracted were fractionated into neutral lipids and glycolipids with use of Sephadex A-25 column (of the acetate form). The glycolipids were chemically neutralized with weak alkali and the resultant substance was desalted by dialysis and subsequent treatment with an ion-exchange resin and was thereafter lyophilized, with the result that 0.2 mg of gangliosides was obtained as an example of a toxin neutralizer according to the second aspect of the present invention.

Two μg of botulinus toxin of each of the types B and E was mixed with 1 μg and 10 μg of each of the two types of neutralizers thus prepared one from the bovine milk and the other from the commercially available buttermilk. Each of the eight mixtures thus prepared was dissolved in 0.5 ml of 0.01M Tris-HCl buffer (pH 7.2). After reaction at 37° C. for 30 minutes, toxin inactivation ability tests similar to that used in Example 1 were conducted with the eight test samples to determine the amount of residual toxin in each of the samples. The following table shows the results of these tests, wherein "Milk" in the column of "Starting Material" refers to the bovine milk which resulted in a neutralizer according to the first aspect of the present invention and "Buttermilk" in the same column refers to the commercially available buttermilk which resulted in a neutralizer according to the second aspect of the present invention.

| Type of Toxin | Starting Material | Quantity of Neutralizer (μg) | Residual Toxin (%) |
| --- | --- | --- | --- |
| B | Milk | 1 | 57.8 |
|   |      | 10 | 2.2 |
| B | Buttermilk | 1 | 5.7 |
|   |            | 10 | 1.5 |
| E | Milk | 1 | Less than 2.0 |
|   |      | 10 | Less than 2.0 |
| E | Buttermilk | 1 | 29.5 |
|   |            | 10 | 24.6 |

What is claimed is:

1. A botulinus toxin neutralizer comprising heat-treated fat globule membranes of animal milk.

2. A botulinus toxin neutralizer comprising gangliosides isolated from fat globule membranes of animal milk.

3. A method of preparing a botulinus toxin neutralizer from a material containing fat globules of animal milk, comprising the steps of
   (a) fractionating said material for separating the membranes of said fat globules from the rest of the material, and
   (b) subjecting the separated fat globule membranes to heat treatment.

4. A method of preparing a botulinus toxin neutralizer as set forth in claim 3, in which animal milk is used as said material, said fat globule membranes being separated from the rest of the animal milk by fractionating the animal milk to separate cream from the rest of the animal milk, washing the cream to remove impurities therefrom, churning the resultant cream to separate the cream into buttermilk and butter granules, and fractionating the buttermilk to separate the globule membranes from the rest of the buttermilk.

5. A method of preparing a botulinus toxin neutralizer as set forth in claim 3, in which buttermilk is used as said material, said fat globule membranes being separated from the rest of the buttermilk by extractig whole lipids from the buttermilk, fractionating the lipids into a neutral lipid fraction and a glycolipid fraction and chemically neutralizing the glycolipid fraction.

6. A method of preparing a botulinus toxin neutralizer from a material containing fat globules, comprising the steps of
   (a) fractionating said material for separating the membranes of said fat globules from the rest of the material, and
   (b) isolating gangliosides from said globule membranes.

7. A method of preparing a botulinus toxin neutralizer as set forth in claim 6, in which animal milk is used as said material, said fat globule membranes being separated from the rest of the animal milk by fractionating the animal milk to separate cream from the rest of the animal milk, washing the cream to remove impurities therefrom, churning the resultant cream to separate the cream into buttermilk and butter granules, and fractionating the buttermilk to separate the globule membranes from the rest of the buttermilk.

8. A method of preparing a botulinus toxin neutralizer as set forth in claim 7, in which said gangliosides are isolated from said fat globule membranes by extracting whole lipids from the buttermilk, fractionating the lipids into a neutral lipid fraction and a glycolipid fraction and chemically neutralizing the glycolipid fraction.

9. A method of preparing a botulinus toxin neutralizer as set forth in claim 3, in which said fat globule membranes are purified before they are subjected to said heat treatment.

10. A method of preparing a botulinus toxin neutralizer as set forth in claim 3, in which said fat globule membranes are disintegrated before they are subjected to said heat treatment.

11. A method of preparing a botulinus toxin neutralizer as set forth in claim 3, in which said fat globule membranes are purified and disintegrated before they are subjected to said heat treatment.

12. A method of preparing a botulinus toxin neutralizer as set forth in claim 3, in which said fat globule membranes are lyophilized before they are subjected to said heat treatment.

13. A method of preparing a botulinus toxin neutralizer as set forth in claim 3, in which said fat globule membranes are purified and lyophilized before they are subjected to said heat treatment.

14. A method of preparing a botulinus toxin neutralizer as set forth in claim 3, in which said fat globule membranes are lyophilized and disintegrated before they are subjected to said heat treatment.

15. A method of preparing a botulinus toxin neutralizer as set forth in claim 3, in which said fat globule membranes are purified, lyophilized and disintegrated before they are subjected to said heat treatment.

16. A method of preparing a botulinus toxin neutralizer as set forth in any one of claims 9, 11, 13 and 15, in which said fat globule membranes are purified by dialysis.

17. A method of preparing a botulinus toxin neutralizer as set forth in any one of claims 9, 11, 13 and 15, in which said fat globule membranes are purified by ammonia sulfate fractionation.

18. A method of preparing a botulinus toxin neutralizer as set forth in any one of claims 9, 11, 13 and 15, in which said fat globule membranes are purified by gel filtration.

19. A method of preparing a botulinus toxin neutralizer as set forth in any one of claims 9, 11, 13 and 15, in which said fat globule membranes are purified by isoelectric-point precipitation.

20. A method of preparing a botulinus toxin neutralizer as set forth in any one of claims 9 to 15, in which said fat globule membranes are disintegrated by ultrasonication.

21. A method of preparing a botulinus toxin neutralizer as set forth in any one of claims 9 to 15, in which said fat globule membranes are copresent with enzymes in said material, said separated fat globule membranes being heated to a temperature selected to inactivate said enzymes during said heat treatment.

* * * * *